(12) United States Patent
Edgington et al.

(10) Patent No.: US 8,377,489 B2
(45) Date of Patent: Feb. 19, 2013

(54) BANANA TREATMENTS

(75) Inventors: Todd Bryan Edgington, Wenatchee, WA (US); Timothy Malefyt, Stroudsburg, PA (US); Alvaro R. Ureña-Padilla, Cartago (CR)

(73) Assignee: Rohm and Haas Company, Philadelphia, PA (US)

( * ) Notice: Subject to any disclaimer, the term of this patent is extended or adjusted under 35 U.S.C. 154(b) by 422 days.

(21) Appl. No.: 12/583,406

(22) Filed: Aug. 20, 2009

(65) Prior Publication Data

US 2010/0047408 A1 Feb. 25, 2010

Related U.S. Application Data

(60) Provisional application No. 61/189,995, filed on Aug. 25, 2008.

(51) Int. Cl.
*A23C 9/14* (2006.01)
(52) U.S. Cl. ......... 426/271; 504/114; 426/330; 426/323
(58) Field of Classification Search .................. 426/271
See application file for complete search history.

(56) References Cited

U.S. PATENT DOCUMENTS

| 4,857,333 | A | * | 8/1989 | Harold ........................... 424/442 |
| 5,518,988 | A | | 5/1996 | Sisler |
| 6,017,849 | A | | 1/2000 | Daly |
| 2004/0072694 | A1 | | 4/2004 | Jacobson |
| 2005/0261131 | A1 | | 11/2005 | Basel et al. |
| 2005/0261132 | A1 | | 11/2005 | Kostansek |
| 2007/0265166 | A1 | * | 11/2007 | Bardella et al. ............... 504/357 |
| 2009/0035380 | A1 | | 2/2009 | Kostansek |

FOREIGN PATENT DOCUMENTS

| EP | 1237411 | 9/2002 |
| EP | 1566107 | 8/2005 |
| EP | 1597968 | 11/2005 |
| EP | 1782692 | 5/2007 |
| EP | 2 020 177 A1 | 2/2009 |

OTHER PUBLICATIONS

Everts: Reining In Ripening; Chemical & Engineering News; Oct. 29, 2007, vol. 85, No. 44, pp. 10-15.*
Neon: Kinetics of Molecular Encapsulation of 1-Methylcyclopropene into r-Cyclodextrin; 11020 J. Agric. Food Chem. 2007, 55, 11020-11026.*
Choi: Influence of aqueous 1-methylcyclopropene concentration, immersion duration, and solution longevity on the postharvest ripening of breaker-turning tomato (*Solanum lycopersicum* L.) fruit; Postharvest Biology and Technology 49 (2008) 147-154; accepted Jan. 3, 2008.*
Manganaris: Effect of Dips in a 1-Methylcyclopropene-Generating Solution on 'Harrow Sun' Plums Stored under Different Temperature Regimes; J. Agric. Food Chem. 2007, 55, 7015-7020.*
Watkins: Overview of 1-Methylcyclopropene Trials and Uses for Edible Horticultural Crops; Hortscience vol. 43(1) Feb. 2008.*

* cited by examiner

*Primary Examiner* — Patricia George
(74) *Attorney, Agent, or Firm* — Yung Il Lee; TaskBritt, P.C.

(57) ABSTRACT

There is provided a method for treating bananas comprising contacting said bananas with a liquid composition comprising a cyclopropene molecular encapsulation agent complex, wherein the duration of said contacting is from 1 second to 4 minutes.

13 Claims, No Drawings

BANANA TREATMENTS

This application claims the benefit of priority under 35 U.S.C. §119(e) of U.S. Provisional Patent Application No. 61/189,995 filed on Aug. 25, 2008.

BACKGROUND

It is common to harvest and then ship bananas while the peels are green. It is also common, once the bananas have reached a location near where they will be sold, to place them in an enclosed volume and expose them to ethylene gas. After the exposure to ethylene, the normally ripen more quickly. As the bananas ripen, the peels gradually turn yellow; the peels remain yellow for some time; then the peels develop black spots; and eventually the bananas become undesirably over-ripe.

Bananas are prone to various problems. One such problem is premature ripening, which sometimes occurs during shipment. It is desired that the bananas have a green life (i.e., the time during which they remain green) that is longer than the shipping time. Sometimes, events can shorten the green life of bananas. For example, if, during shipment, the interior of a container of bananas is exposed to ethylene gas, many of the bananas will ripen prior to arrival at their destination, and many of those bananas will need to be discarded. This premature ripening causes significant losses to the banana industry.

The problem of premature ripening is exacerbated if the bananas were stressed prior to harvest. Stress can arise from a variety of causes, including, for example, flooding or disease (such as, for example, black Sigatoka) or other stress factors or combinations thereof. It is considered that stressed bananas will normally have a shortened green life. Commonly, when stress is observed, the bananas are harvested early, which helps to extend the green life, but the early harvesting causes a reduction in size of the bananas and in crop yield.

Another common problem is that bananas have a relatively short yellow life. That is, while bananas are on display in a retail setting, they are desirable to consumers during their "yellow life" (i.e., from the time the peels start to turn yellow until the bananas become over-ripe). Because the yellow life is often very short, many bananas reach the end of their yellow life before they are sold and have to be discarded, which also causes losses to the banana industry.

US 2005/0261132 discloses treating plants or plant parts with liquid composition containing metal-complexing agent. It is desired to provide a method of treating bananas in particular that will improve the green life or the yellow life or both. It is also desired to provide a method that can be used to treat bananas that were stressed during harvest and can thereby overcome the necessity of harvesting such bananas early.

STATEMENT OF THE INVENTION

In a first aspect of the present invention, there is provided a method for treating bananas comprising contacting said bananas with a liquid composition comprising a cyclopropene molecular encapsulation agent complex, wherein the duration of said contacting is from 1 second to 4 minutes.

DETAILED DESCRIPTION

As used herein, "banana" refers to any member of the genus *Musa*, including, for example, bananas and plantains.

As used herein, when bananas are said to be "treated," it is meant that the bananas are brought into contact with the liquid composition of the present invention.

The practice of the present invention involves the use of one or more cyclopropenes. As used herein, "a cyclopropene" is any compound with the formula

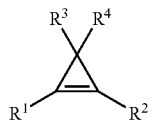

where each $R^1$, $R^2$, $R^3$ and $R^4$ is independently selected from the group consisting of H and a chemical group of the formula:

$$-(L)_n-Z$$

where n is an integer from 0 to 12. Each L is a bivalent radical. Suitable L groups include, for example, radicals containing one or more atoms selected from H, B, C, N, O, P, S, Si, or mixtures thereof. The atoms within an L group may be connected to each other by single bonds, double bonds, triple bonds, or mixtures thereof. Each L group may be linear, branched, cyclic, or a combination thereof. In any one R group (i.e., any one of $R^1$, $R^2$, $R^3$ and $R^4$) the total number of heteroatoms (i.e., atoms that are neither H nor C) is from 0 to 6. Independently, in any one R group the total number of non-hydrogen atoms is 50 or less. Each Z is a monovalent radical. Each Z is independently selected from the group consisting of hydrogen, halo, cyano, nitro, nitroso, azido, chlorate, bromate, iodate, isocyanato, isocyanido, isothiocyanato, pentafluorothio, and a chemical group G, wherein G is a 3 to 14 membered ring system.

The $R^1$, $R^2$, $R^3$, and $R^4$ groups are independently selected from the suitable groups. The $R^1$, $R^2$, $R^3$, and $R^4$ groups may be the same as each other, or any number of them may be different from the others. Among the groups that are suitable for use as one or more of $R^1$, $R^2$, $R^3$, and $R^4$ are, for example, aliphatic groups, aliphatic-oxy groups, alkylphosphonato groups, cycloaliphatic groups, cycloalkylsulfonyl groups, cycloalkylamino groups, heterocyclic groups, aryl groups, heteroaryl groups, halogens, silyl groups, other groups, and mixtures and combinations thereof. Groups that are suitable for use as one or more of $R^1$, $R^2$, $R^3$, and $R^4$ may be substituted or unsubstituted. Independently, groups that are suitable for use as one or more of $R^1$, $R^2$, $R^3$, and $R^4$ may be connected directly to the cyclopropene ring or may be connected to the cyclopropene ring through an intervening group such as, for example, a heteroatom-containing group.

Among the suitable $R^1$, $R^2$, $R^3$, and $R^4$ groups are, for example, aliphatic groups. Some suitable aliphatic groups include, for example, alkyl, alkenyl, and alkynyl groups. Suitable aliphatic groups may be linear, branched, cyclic, or a combination thereof. Independently, suitable aliphatic groups may be substituted or unsubstituted.

As used herein, a chemical group of interest is said to be "substituted" if one or more hydrogen atoms of the chemical group of interest is replaced by a substituent. It is contemplated that such substituted groups may be made by any method, including but not limited to making the unsubstituted form of the chemical group of interest and then performing a substitution. Suitable substituents include, for example, alkyl, alkenyl, acetylamino, alkoxy, alkoxyalkoxy, alkoxycarbonyl, alkoxyimio, carboxy, halo, haloalkoxy, hydroxy, alkylsulfonyl, alkylthio, trialkylsilyl, dialkylamino, and combinations thereof. An additional suitable substituent, which, if present, may be present alone or in combination with another suitable substituent, is $$-(L)_m-Z$$

where m is 0 to 8, and where L and Z are defined herein above. If more than one substituent is present on a single chemical group of interest, each substituent may replace a different hydrogen atom, or one substituent may be attached to another substituent, which in turn is attached to the chemical group of interest, or a combination thereof.

Among the suitable $R^1$, $R^2$, $R^3$, and $R^4$ groups are, for example, substituted and unsubstituted aliphatic-oxy groups, such as, for example, alkenoxy, alkoxy, alkynoxy, and alkoxycarbonyloxy.

Also among the suitable $R^1$, $R^2$, $R^3$, and $R^4$ groups are, for example, substituted and unsubstituted alkylphosphonato, substituted and unsubstituted alkylphosphato, substituted and unsubstituted alkylamino, substituted and unsubstituted alkylsulfonyl, substituted and unsubstituted alkylcarbonyl, and substituted and unsubstituted alkylaminosulfonyl, including, for example, alkylphosphonato, dialkylphosphato, dialkylthiophosphato, dialkylamino, alkylcarbonyl, and dialkylaminosulfonyl.

Also among the suitable $R^1$, $R^2$, $R^3$, and $R^4$ groups are, for example, substituted and unsubstituted cycloalkylsulfonyl groups and cycloalkylamino groups, such as, for example, dicycloalkylaminosulfonyl and dicycloalkylamino.

Also among the suitable $R^1$, $R^2$, $R^3$, and $R^4$ groups are, for example, substituted and unsubstituted heterocyclyl groups (i.e., aromatic or non-aromatic cyclic groups with at least one heteroatom in the ring).

Also among the suitable $R^1$, $R^2$, $R^3$, and $R^4$ groups are, for example, substituted and unsubstituted heterocyclyl groups that are connected to the cyclopropene compound through an intervening oxy group, amino group, carbonyl group, or sulfonyl group; examples of such $R^1$, $R^2$, $R^3$, and $R^4$ groups are heterocyclyloxy, heterocyclylcarbonyl, diheterocyclylamino, and diheterocyclylaminosulfonyl.

Also among the suitable $R^1$, $R^2$, $R^3$, and $R^4$ groups are, for example, substituted and unsubstituted aryl groups. Suitable substituents are those described herein above. In some embodiments, one or more substituted aryl group is used in which at least one substituent is one or more of alkenyl, alkyl, alkynyl, acetylamino, alkoxyalkoxy, alkoxy, alkoxycarbonyl, carbonyl, alkylcarbonyloxy, carboxy, arylamino, haloalkoxy, halo, hydroxy, trialkylsilyl, dialkylamino, alkylsulfonyl, sulfonylalkyl, alkylthio, thioalkyl, arylaminosulfonyl, and haloalkylthio.

Also among the suitable $R^1$, $R^2$, $R^3$, and $R^4$ groups are, for example, substituted and unsubstituted heterocyclic groups that are connected to the cyclopropene compound through an intervening oxy group, amino group, carbonyl group, sulfonyl group, thioalkyl group, or aminosulfonyl group; examples of such $R^1$, $R^2$, $R^3$, and $R^4$ groups are diheteroarylamino, heteroarylthioalkyl, and diheteroarylaminosulfonyl.

Also among the suitable $R^1$, $R^2$, $R^3$, and $R^4$ groups are, for example, hydrogen, fluoro, chloro, bromo, iodo, cyano, nitro, nitroso, azido, chlorato, bromato, iodato, isocyanato, isocyanido, isothiocyanato, pentafluorothio; acetoxy, carboethoxy, cyanato, nitrato, nitrito, perchlorato, allenyl; butylmercapto, diethylphosphonato, dimethylphenylsilyl, isoquinolyl, mercapto, naphthyl, phenoxy, phenyl, piperidino, pyridyl, quinolyl, triethylsilyl, trimethylsilyl; and substituted analogs thereof.

As used herein, the chemical group G is a 3 to 14 membered ring system. Ring systems suitable as chemical group G may be substituted or unsubstituted; they may be aromatic (including, for example, phenyl and napthyl) or aliphatic (including unsaturated aliphatic, partially saturated aliphatic, or saturated aliphatic); and they may be carbocyclic or heterocyclic. Among heterocyclic G groups, some suitable heteroatoms are, for example, nitrogen, sulfur, oxygen, and combinations thereof. Ring systems suitable as chemical group G may be monocyclic, bicyclic, tricyclic, polycyclic, spiro, or fused; among suitable chemical group G ring systems that are bicyclic, tricyclic, or fused, the various rings in a single chemical group G may be all the same type or may be of two or more types (for example, an aromatic ring may be fused with an aliphatic ring).

In some embodiments, G is a ring system that contains a saturated or unsaturated 3 membered ring, such as, for example, a substituted or unsubstituted cyclopropane, cyclopropene, epoxide, or aziridine ring.

In some embodiments, G is a ring system that contains a 4 membered heterocyclic ring; in some of such embodiments, the heterocyclic ring contains exactly one heteroatom. Independently, in some embodiments, G is a ring system that contains a heterocyclic ring with 5 or more members; in some of such embodiments, the heterocyclic ring contains 1 to 4 heteroatoms. Independently, in some embodiments, the ring in G is unsubstituted; in other embodiments, the ring system contains 1 to 5 substituents; in some of the embodiments in which G contains substituents, each substituent is independently chosen from the substituents described herein above. Also suitable are embodiments in which G is a carbocyclic ring system.

In some embodiments, each G is independently a substituted or unsubstituted phenyl, pyridyl, cyclohexyl, cyclopentyl, cycloheptyl, pyrolyl, furyl, thiophenyl, triazolyl, pyrazolyl, 1,3-dioxolanyl, or morpholinyl. Among these embodiments include those embodiments, for example, in which G is unsubstituted or substituted phenyl, cyclopentyl, cycloheptyl, or cyclohexyl. In some of these embodiments, G is cyclopentyl, cycloheptyl, cyclohexyl, phenyl, or substituted phenyl. Among embodiments in which G is substituted phenyl are embodiments, for example, in which there are 1, 2, or 3 substituents. Independently, also among embodiments in which G is substituted phenyl are embodiments, for example, in which the substituents are independently selected from methyl, methoxy, and halo.

Also contemplated are embodiments in which $R^3$ and $R^4$ are combined into a single group, which is attached to the number 3 carbon atom of the cyclopropene ring by a double bond. Some of such compounds are described in US Patent Publication 2005/0288189.

In some embodiments, one or more cyclopropenes are used in which one or more of $R^1$, $R^2$, $R^3$, and $R^4$ is hydrogen. In some embodiments, $R^1$ or $R^2$ or both $R^1$ and $R^2$ is hydrogen. Independently, in some embodiments, $R^3$ or $R^4$ or both $R^3$ and $R^4$ is hydrogen. In some embodiments, $R^2$, $R^3$, and $R^4$ are hydrogen.

In some embodiments, one or more of $R^1$, $R^2$, $R^3$, and $R^4$ is a structure that has no double bond. Independently, in some embodiments, one or more of $R^1$, $R^2$, $R^3$, and $R^4$ is a structure that has no triple bond. Independently, in some embodiments, one or more of $R^1$, $R^2$, $R^3$, and $R^4$ is a structure that has no halogen atom substituent. Independently, in some embodiments, one or more of $R^1$, $R^2$, $R^3$, and $R^4$ is a structure that has no substituent that is ionic.

In some embodiments, one or more of $R^1$, $R^2$, $R^3$, and $R^4$ is hydrogen or $(C_1-C_{10})$ alkyl. In some embodiments, each of $R^1$, $R^2$, $R^3$, and $R^4$ is hydrogen or $(C_1-C_8)$ alkyl. In some embodiments, each of $R^1$, $R^2$, $R^3$, and $R^4$ is hydrogen or ($C_1$-$C_4$) alkyl. In some embodiments, each of $R^1$, $R^2$, $R^3$, and $R^4$ is hydrogen or methyl. In some embodiments, $R^1$ is ($C_1$-$C_4$) alkyl and each of $R^2$, $R^3$, and $R^4$ is hydrogen. In some embodiments, $R^1$ is methyl and each of $R^2$, $R^3$, and $R^4$ is hydrogen, and the cyclopropene is known herein as "1-MCP."

In some embodiments, a cyclopropene is used that has boiling point at one atmosphere pressure of 50° C. or lower; or 25° C. or lower; or 15° C. or lower. Independently, in some embodiments, a cyclopropene is used that has boiling point at one atmosphere pressure of −100° C. or higher; −50° C. or higher; or −25° C. or higher; or 0° C. or higher.

The cyclopropenes applicable to this invention may be prepared by any method. Some suitable methods of preparation of cyclopropenes are the processes disclosed in U.S. Pat. Nos. 5,518,988 and 6,017,849.

The composition of the present invention includes at least one molecular encapsulating agent. Suitable molecular encapsulating agents include, for example, organic and inorganic molecular encapsulating agents. Suitable organic molecular encapsulating agents include, for example, substituted cyclodextrins, unsubstituted cyclodextrins, and crown ethers. Suitable inorganic molecular encapsulating agents include, for example, zeolites. Mixtures of suitable molecular encapsulating agents are also suitable. In some embodiments of the invention, the encapsulating agent is alpha-cyclodextrin, beta-cyclodextrin, gamma-cyclodextrin, or a mixture thereof. In some embodiments of the invention, particularly when the cyclopropene is 1-methylcyclopropene, the encapsulating agent is alpha-cyclodextrin. The preferred encapsulating agent will vary depending upon the structure of the cyclopropene or cyclopropenes being used. Any cyclodextrin or mixture of cyclodextrins, cyclodextrin polymers, modified cyclodextrins, or mixtures thereof can also be utilized pursuant to the present invention. Some cyclodextrins are available, for example, from Wacker Biochem Inc., Adrian, Mich., as well as other vendors.

At least one molecular encapsulating agent encapsulates one or more cyclopropenes. A cyclopropene or substituted cyclopropene molecule encapsulated in a molecule of a molecular encapsulating agent is known herein as a "cyclopropene molecular encapsulating agent complex." The cyclopropene molecular encapsulation agent complexes can be prepared by any means. In one method of preparation, for example, such complexes are prepared by contacting the cyclopropene with a solution or slurry of the molecular encapsulation agent and then isolating the complex, using, for example, processes disclosed in U.S. Pat. No. 6,017,849. For example, in one method of making a complex in which 1-MCP is encapsulated in a molecular encapsulating agent, the 1-MCP gas is bubbled through a solution of alpha-cyclodextrin in water, from which the complex first precipitates and is then isolated by filtration. In some embodiments, complexes are made by the above method and, after isolation, are dried and stored in solid form, for example as a powder, for later addition to useful compositions.

The amount of molecular encapsulating agent can usefully be characterized by the ratio of moles of molecular encapsulating agent to moles of cyclopropene. In some embodiments, the ratio of moles of molecular encapsulating agent to moles of cyclopropene is 0.1 or larger; or 0.2 or larger; or 0.5 or larger; or 0.9 or larger. Independently, in some of such embodiments, the ratio of moles of molecular encapsulating agent to moles of cyclopropene is 2 or lower; or 1.5 or lower.

The practice of the present invention involves one or more liquid compositions. Liquid compositions are liquid at 25° C. In some embodiments, liquid compositions are liquid at the temperature at which the composition is used to treat bananas. Because bananas are often treated outside of any buildings or in buildings that are not temperature-controlled, bananas may be treated at temperatures ranging from 1° C. to 45° C.; suitable liquid compositions need not be liquid over that entire range, but suitable liquid compositions are liquid at least at some temperature from 1° C. to 45° C.

If a liquid composition contains more than one substance, that liquid composition may be a solution or a dispersion or a combination thereof. If, in the liquid composition, one substance is dispersed in another substance in the form of a dispersion, the dispersion may be of any type, including, for example, a slurry, a suspension, a latex, an emulsion, a miniemulsion, a microemulsion, or any combination thereof.

In some embodiments, the amount of cyclopropene in the liquid composition is 0.1 microgram per liter or more; or 0.2 microgram per liter or more; or 0.5 microgram per liter or more; or 1 microgram per liter or more; or 2 microgram per liter or more; or 4 microgram per liter or more. Independently, in some embodiments, the amount of cyclopropene in the liquid composition is 1,000 microgram per liter or less; or 500 microgram per liter or less; or 200 microgram per liter or less; or 100 microgram per liter or less.

In some embodiments, the composition of the present invention includes no metal chelating agents. In some embodiments, one or more compositions of the present invention includes one or more metal chelating agents.

A metal chelating agent is a compound, each molecule of which is capable of forming two or more coordinate bonds with a single metal atom. Some metal chelating agents form coordinate bonds with metal atoms because the metal chelating agents contain electron-donor atoms that participate in coordinate bonds with metal atoms. Suitable chelating agents include, for example, organic and inorganic chelating agents. Among the suitable inorganic chelating agents are, for example, phosphates such as, for example, tetrasodium pyrophosphate, sodium tripolyphosphate, and hexametaphosphoric acid. Among the suitable organic chelating agents are those with macrocyclic structures and non-macrocyclic structures. Among the suitable macrocyclic organic chelating agents are, for example, porphine compounds, cyclic polyethers (also called crown ethers), and macrocyclic compounds with both nitrogen and oxygen atoms.

Some suitable organic chelating agents that have non-macrocyclic structures are, for example, aminocarboxylic acids, 1,3-diketones, hydroxycarboxylic acids, polyamines, aminoalcohols, aromatic heterocyclic bases, phenol, aminophenols, oximes, Shiff bases, sulfur compounds, and mixtures thereof. In some embodiments, the chelating agent includes one or more aminocarboxylic acids, one or more hydroxycarboxylic acids, one or more oximes, or a mixture thereof. Some suitable aminocarboxylic acids include, for example, ethylenediaminetetraacetic acid (EDTA), hydroxyethylethylenediaminetriacetic acid (HEDTA), nitrilotriacetic acid (NTA), N-dihydroxyethylglycine (2-HxG), ethylenebis(hydroxyphenylglycine) (EHPG), and mixtures thereof. Some suitable hydroxycarboxylic acids include, for example, tartaric acid, citric acid, gluconic acid, 5-sulfosalicylic acid, and mixtures thereof. Some suitable oximes include, for example, dimethylglyoxime, salicylaldoxime, and mixtures thereof. In some embodiments, EDTA is used.

Among embodiments in which a chelating agent is used that is an acid, the acid may be present in neutral form or in the form of a salt or in a combination thereof. Salts may have any counterion, including, for example, sodium, potassium, magnesium, calcium, or mixtures thereof. In some embodiments, magnesium or calcium or a mixture thereof is used.

Some additional suitable chelating agents are polymeric. Some suitable polymeric chelating agents include, for example, polyethyleneimines, polymethacryloylacetones, poly(acrylic acid), and poly(methacrylic acid). Poly(acrylic acid) is used in some embodiments.

Mixtures of suitable metal-complexing agents are also suitable.

Independently, in some embodiments in which a liquid composition that includes water is used, and in which the liquid composition contains one or more metal-complexing agent, the amount of metal-complexing agent can usefully be characterized by the molar concentration of metal-complexing agent in the liquid composition (i.e., moles of metal-complexing agent per liter of liquid composition). In some of such liquid compositions, the concentration of metal-complexing agent is 0.00001 mM (i.e., milli-Molar) or greater; or 0.0001 mM or greater; or 0.001 mM or greater; or 0.01 mM or greater; or 0.1 mM or greater. Independently, in some embodiments in which a liquid composition of the present invention includes water, the concentration of metal-complexing agent is 100 mM or less; or 10 mM or less; or 1 mM or less.

In some embodiments, the liquid composition of the present invention is aqueous. As used herein, a composition is aqueous if it contains 50% or more water by weight based on the weight of the composition. In some embodiments, the liquid composition of the present invention contains water in the amount, by weight based on the weight of the composition, 75% or more; or 85% or more; or 95% or more.

In some embodiments, the composition of the present invention contains little or no nonionic surfactant. That is, the composition either contains no nonionic surfactant, or, if any nonionic surfactant is present, the amount of nonionic surfactant is, by weight based on the weight of the composition, 0.1% or less; or 0.01% or less; or 0.002% or less. Nonionic surfactants include, for example, alkyl polyoxyalkylene nonionic surfactants, aryl polyoxyalkylene nonionic surfactants, and polyoxyalkylene block copolymer nonionic surfactants.

In some embodiments, the composition of the present invention contains little or no surfactant of any type (i.e., nonionic, anionic, or cationic); "little or no" is defined herein above.

The bananas treated in the practice of the present invention may be any members of the genus *Musa*. In some embodiments of the present invention edible fruits of the genus *Musa* are treated. In some embodiments, plantains or bananas that are not plantains are treated. In some embodiments, bananas that are not plantains are treated. In some embodiments, bananas of the species *M. acuminata* Colla or the hybrid *M. X paradisiaca* L. are treated. In some embodiments, members of one or more of the following varieties of banana are treated: Sucrier, Lady Finger, Gros Michel, Cavendish (including, for example, Dwarf Cavendish, Giant Cavendish, Pisang masak hijau, Robusta, or Valery), Bluggoe, Ice Cream, Mysore, Salembale, Rasabale, Pachabale, Chandrabale, Silk, Red, Fehi, Golden Beauty, or Orinoco. In some embodiments, one or more variety of plantains is treated, including, for example, French plantain, Horn plantain, Maaricongo, Common Dwarf, Pelipita, Saba, Harton, Dominico-Harton, or Currare.

Bananas are normally harvested by cutting the bunch of bananas from the pseudostem on which it grew. Subsequent to harvest, bunches are often broken down into smaller connected groups called hands. Bananas may be treated according the present invention as bunches, hands, smaller collections, or individual bananas.

In some embodiments of the present invention, bananas are treated 20 weeks or less after harvest.

In some embodiments of the present invention, bananas are treated 36 hours or less after harvest (i.e., after the bunch is separated from the pseudostem). In some embodiments, the time from harvest until treatment is 24 hours or less; or 10 hours or less; or 3 hours or less; or 1 hour or less; or 20 minutes or less.

In the practice of the present invention, bananas may be brought into contact with the liquid composition by any method. For example, bananas may be brought into contact with the liquid composition by dipping, spraying, drenching, brush-applying, or a combination thereof. In some embodiments, contact is performed by dipping. When dipping is used, bananas are submerged in the liquid composition deeply enough to cover the fruit portion. In a dipping operation, bananas remain submerged for at least 1 second; or at least 2 seconds; or at least 5 seconds; or at least 10 seconds. Independently, in some embodiments employing a dipping operation, bananas remain submerged for 5 minutes or less; or 4 minutes or less; or 2 minutes or less.

In some embodiments, bananas are treated that were exposed to stress prior to harvest. In some cases, stress is caused by, for example, flooding or disease. In some of such embodiments, it is contemplated to harvest the stressed bananas at the growth stage at which they would normally have been harvested if they had not been stressed and to treat the stressed bananas according to the methods of the present invention. Independently, it is contemplated in some embodiments involving stressed bananas, to treat the stressed bananas using liquid composition with concentration of cyclopropene of 35 microgram per liter to 100 microgram per liter.

In some embodiments in which the bananas are not stressed, bananas are contacted with liquid composition having concentration of cyclopropene of less than 35 microgram per liter. In some embodiments in which bananas have been stressed, bananas are contacted with liquid composition having concentration of cyclopropene of more than 35 microgram per liter.

It is to be understood that for purposes of the present specification and claims that the range and ratio limits recited herein can be combined. For example, if ranges of 60 to 120 and 80 to 110 are recited for a particular parameter, it is understood that the ranges of 60 to 110 and 80 to 120 are also contemplated. As a further, independent, example, if a particular parameter is disclosed to have suitable minima of 1, 2, and 3, and if that parameter is disclosed to have suitable maxima of 9 and 10, then all the following ranges are contemplated: 1 to 9, 1 to 10, 2 to 9, 2 to 10, 3 to 9, and 3 to 10.

It is to be understood that for purposes of the present specification and claims that each operation disclosed herein is performed at 25° C. unless otherwise specified.

EXAMPLES

The following Examples, the color of banana peels is rated according to a seven stage rating scale, published by Chiquita Brands International, Inc. (http://www.chiquita.com/chiquita/Discover/cbripen.asp): stage 1 (dark green); stage 2 (all light green); stage 3 (more green than yellow); stage 4 (more yellow than green); stage 5 (green tips and necks); stage 6 (all yellow; maybe light green necks, no green tips); stage 7 (yellow flecked with brown). Consumers generally prefer to eat bananas in stage 5 or stage 6.

Comparative Example 1

Banana fruit with an age of 12 weeks, grown and treated in Costa Rica. The bananas were dipped (not sprayed). The solution of every 1-MCP treatment included 0.6 ml/l NuFilm 17® 96% (elastomer-forming additive, Miller Chemical and Fertilizer Co.). Control sample had no dip. Other samples were dipped in water solution in which powdered encapsulation complex of 1-MCP in alpha-cyclodextrin was added to water to give concentration of 20 microgram 1-MCP per liter. Bananas were dipped for zero time (in and out), 5 minutes, or 20 minutes.

After 1-MCP treatment, fruit were allowed to dry on racks after treatments before being repacked in the boxes. The boxes were stored at 14° C. for 7 days. The boxes were conditioned at 20-21° C. for 6 hours before being treated with a continuous stream of 100 microliter per liter ethylene in a treatment chamber at 20° C. by 24 hours. After ethylene treatment the boxes were kept at ambient conditions (20° C. and 95% RH). Bananas were inspected at 5, 7, 10, and 12 days after exposure to ethylene.

Complete randomized design was used, with 4 treatments and 2 boxes per treatment. Clusters from each treatment were evaluated every two days after ethylene treatment.

Bananas dipped for 5 minutes or 20 minutes did not ripen normally. They remained green after 12 days.

No significant difference in ripening was observed between the control bananas and the bananas dipped in and out quickly.

Example 2

Bananas (Cavendish *Musa* spp.) were dipped in water solutions as listed below. Solutions containing 1-MCP were prepared by adding powdered encapsulation complex of 1-MCP in alpha-cyclodextrin to water to give concentration of 20 microgram 1-MCP per liter. Duration of dip was 15 seconds.

Bananas were 12 weeks of age, grown and tested in Costa Rica. After dipping, bananas were dried on racks and packed in boxes. Boxes were stored at 14° C. of 9 days, then conditioned at 20-21 ° C. for 6 hours, then exposed to continuous stream of 100 microliter per liter of ethylene in a chamber at 21° C. for 24 hours; then kept at ambient conditions (20° C. and 80% relative humidity (RH)).

Randomized design was used, with 10 treatments and 1 box per treatment. Clusters from each treatment were evaluated daily after ethylene treatment. Peel color was evaluated as described above. Severity of sugar spots was rated according to the percentage of bananas showing sugar spots as follows: 1 (none); 2 (0-5%); 3 (5-10%); 4 (10-25%); 5 (25-50%); 6 (50-100%).

Peel Color Ratings were as Follows:

| Treatment | 1-MCP (ppb) | days after ethylene exposure | | | | | | |
|---|---|---|---|---|---|---|---|---|
| | | 1 | 2 | 3 | 6 | 7 | 8 | 9 |
| water | 0 | 2.5 | 3 | 3 | 4.5 | 5 | 5 | 6 |
| water | 20 | 2 | 2 | 2 | 2.5 | 2.5 | 3 | 3 |
| NuFilm ™[1] | 0 | 2 | 3 | 3 | 5 | 5 | 5 | 6 |
| NuFilm ™ | 20 | 2 | 2 | 2 | 2 | 2 | 2 | 2.5 |
| NP-7[2] | 0 | 2 | 2.5 | 3 | 4.5 | 4.5 | 5 | 5.5 |
| NP-7 | 20 | 2 | 2.5 | 3 | 4 | 4.5 | 5 | 5.5 |
| Mineral Oil | 0 | 2 | 2 | 2 | 2 | 2 | 2 | 2.5 |
| Mineral Oil | 20 | 2 | 2 | 2 | 2 | 2 | 2 | 2 |
| Tween ™ 80[3] | 0 | 2.5 | 2.5 | 3 | 4 | 4 | 4.5 | 5 |
| Tween ™ 80 | 20 | 2 | 2.5 | 2.5 | 3.5 | 4 | 4 | 5 |

[1]elastomeric film former from Miller Chemical and Fertilizer Co.
[2]Tergitol ™ nonionic surfactant from Dow Chemical Co.
[3]nonionic surfactant from ICI Americas, Inc.

Sugar Spot Ratings were as Follows:

| Treatment | 1-MCP (ppb) | days after ethylene exposure | | | | | | |
|---|---|---|---|---|---|---|---|---|
| | | 1 | 2 | 3 | 6 | 7 | 8 | 9 |
| water | 0 | 1 | 1 | 1 | 1 | 1 | 1 | 4 |
| water | 20 | 1 | 1 | 1 | 1 | 1 | 1 | 1 |
| NuFilm ™ | 0 | 1 | 1 | 1 | 1 | 1 | 1 | 2 |
| NuFilm ™ | 20 | 1 | 1 | 1 | 1 | 1 | 1 | 1 |
| NP-7 | 0 | 1 | 1 | 1 | 1 | 1 | 1 | 2 |
| NP-7 | 20 | 1 | 1 | 1 | 1 | 1 | 1 | 2 |
| Mineral Oil | 0 | 1 | 1 | 1 | 1 | 1 | 1 | 1 |
| Mineral Oil | 20 | 1 | 1 | 1 | 1 | 1 | 1 | 1 |
| Tween ™ 80 | 0 | 1 | 1 | 1 | 1 | 1 | 1 | 1 |
| Tween ™ 80 | 20 | 1 | 1 | 1 | 1 | 1 | 1 | 1 |

Bananas dipped in mineral oil did not ripen in the weeks of the test. Treatment with NP-7 had no effect on ripening, with or without 1-MCP. Water with 1-MCP and NuFilm™ with 1-MCP desirably delayed ripening. Bananas treated with Tween™ 80 did not ripen properly with or without 1-MCP. Bananas treated with just water had highest level of sugar spots.

We claim:

1. A method for treating bananas comprising contacting said bananas with a composition comprising a cyclopropene molecular encapsulation agent complex, wherein the composition is in a liquid state,
   wherein a duration of said contacting is from 1 second to 4 minutes,
   wherein said treating is performed after harvest, and
   wherein said treating is performed 20 weeks or less after harvest.

2. The method of claim 1, wherein said liquid composition is aqueous.

3. The method of claim 1, wherein said liquid composition comprises from 0% to 0.1% nonionic surfactant by weight based on a total weight of said liquid composition.

4. The method of claim 1, wherein said liquid composition comprises a metal chelating agent at concentration from 0.1 to 100 millimole per liter.

5. The method of claim 1, wherein contacting said bananas with a liquid composition comprises dipping said bananas in said liquid composition.

6. The method of claim 5, wherein said dipping has duration of 5 to 60 seconds.

7. The method of claim 1, wherein an amount of cyclopropene in said liquid composition is from 5 to 100 microgram per liter.

8. The method of claim 1, wherein said cyclopropene is 1-methyl cyclopropene.

9. The method of claim 1, wherein said molecular encapsulating agent is alpha-cyclodextrin.

10. The method of claim 3, wherein said liquid composition comprises a metal chelating agent at concentration from 0.1 to 100 millimole per liter.

11. The method of claim 3, wherein contacting said bananas with a liquid composition comprises dipping said bananas in said liquid composition, and wherein said dipping has duration of 5 to 60 seconds.

12. The method of claim 1, wherein said bananas are treated subsequent to harvest, wherein said bananas were exposed to disease or flooding prior to harvest, and wherein an amount of cyclopropene in said liquid composition is from 35 to 100 microgram per liter.

13. The method of claim 1, wherein said bananas are treated subsequent to harvest, wherein said bananas were not exposed to disease or flooding prior to harvest, and wherein an amount of cyclopropene in said liquid composition is less than 35 microgram per litter.

* * * * *